United States Patent [19]

Eigler

[11] Patent Number: 4,987,312

[45] Date of Patent: Jan. 22, 1991

[54] PROCESS FOR REPOSITIONING ATOMS ON A SURFACE USING A SCANNING TUNNELING MICROSCOPE

[75] Inventor: Donald M. Eigler, Santa Cruz, Calif.

[73] Assignee: International Business Machines Corporation, Armonk, N.Y.

[21] Appl. No.: 432,657

[22] Filed: Nov. 7, 1989

[51] Int. Cl.5 .............................................. H01J 37/30
[52] U.S. Cl. .............................. 250/492.3; 250/492.2; 369/101; 369/126
[58] Field of Search ......................... 250/492.3, 492.2; 369/101, 126

[56] References Cited

U.S. PATENT DOCUMENTS 4,575,822 3/1986 Quate .................................... 365/174
4,826,732 5/1989 Kazan et al. ......................... 428/432

OTHER PUBLICATIONS

Gomer, IBM Journal of Research and Development, vol. 30, No. 4, Jul. 1986, pp. 428-430.

Primary Examiner—Jack I. Berman
Attorney, Agent, or Firm—Henry E. Otto, Jr.

[57] ABSTRACT

A method is disclosed for repositioning an adsorbate atom or molecule on a substrate surface by moving the tip of a STM to a position adjacent the atom to be moved and subsequently increasing the attraction between the tip and atom by moving the tip closer to the substrate, and then, while the atom remains bound to the surface, moving the tip laterally to drag the atom to a desired position on the surface. The tip is then moved away from the substrate, reducing the attraction between the atom and tip and leaving the atom bound at the desired position.

The atom may be repositioned in close proximity to an atom of the same or another type on the same or a different substrate to create a desired multi-atom structure or synthesize a molecule.

Atoms may also be repositioned to write indicia on a storage medium by dragging atoms into the desired information bearing pattern, for example, by dragging selected atoms out of a respective one of a plurality of parallel atom rows using the tip of a STM to thereby write indicia at locations denoted by the removed atoms.

15 Claims, 1 Drawing Sheet

PROCESS FOR REPOSITIONING ATOMS ON A SURFACE USING A SCANNING TUNNELING MICROSCOPE

This invention relates to a method for repositioning atoms or molecules adsorbed on a substrate, and more particularly to a method using a scanning tunneling microscope (STM) for repositioning an atom or molecule on a substrate, such as for fabricating a multi-atom structure, synthesizing a molecule or recording indicia on a storage medium.

BACKGROUND OF THE INVENTION

Quate U.S. Pat. No. 4,575,822 describes a data storage medium on which, using a STM with a probe tip, indicia are written by forming perturbations on the surface of a substrate. The indicia are then read by scanning over the indicia with the tip of the STM.

The most pertinent prior art of which applicant is aware is Kazan U.S. Pat. No. 4,826,732, which also describes several embodiments of a recording medium. One comprises a substrate having a surface coated with a monolayer of atoms and from which atoms are selectively removed by modulating the input signal to a STM tip to write indicia. Another embodiment comprises a substrate having a surface onto which atoms are selectively deposited to write indicia. In both embodiments, the STM is used to read back information by imaging the surface.

No prior art known to applicant discloses or suggests the repositioning of an atom or molecule from one position on the surface of a substrate to another position on said surface, or the repositioning of atoms or molecules of the same or different type on the same surface to fabricate a desired structure or to synthesize a compound, such as a long-chain copolymer.

SUMMARY OF THE INVENTION

A method is disclosed for repositioning an adsorbate atom (or molecule) on a substrate surface by moving the tip of a STM to a position adjacent the atom to be moved and subsequently increasing the attraction between the tip and atom by moving the tip closer to the substrate; and then, while the atom remains bound to the surface, moving the tip laterally to drag the atom to a desired position on the surface. The tip is then moved away from the substrate, reducing the attraction between the atom and tip and leaving the atom bound at the desired position.

The atom may be repositioned in close proximity to an atom of the same or another type on the substrate to create a desired multi-atom structure or synthesize a molecule.

Atoms may also be repositioned to write indicia on a storage medium by dragging atoms into the desired information bearing pattern, for example, by dragging selected atoms out of a respective one of a plurality of parallel atom rows using the tip of a STM to thereby write indicia at locations denoted by the removed atoms.

Atoms may also be repositioned by lowering the STM tip over the atom to be moved and changing the bias voltage/current until the atom becomes attached to the tip. The tip is retracted, moved laterally and then lowered to reposition the atom on the same or another substrate; whereupon bias voltage/current is changed to leave the atom substrate-bound when the tip is retracted.

DESCRIPTION OF PREFERRED EMBODIMENTS

For simplification of description, the term "atom" as herein used in the specification and claims is intended to define either an atom or a molecule, unless otherwise indicated. Also, since operation of a STM was initially described in U.S. Pat. No. 4,343,993 and is now well-known in the art, its operation will be but briefly described herein.

I

Figure 1:
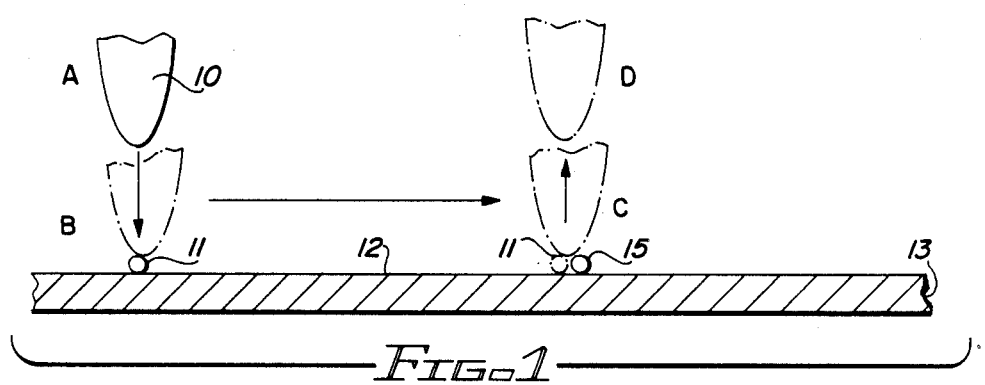
FIG. 1 is a schematic view showing a preferred technique for repositioning an atom on a surface.

A preferred method for repositioning "atoms" is illustrated in FIG. 1. A probe tip 10 of a scanning tunneling microscope (STM) is disposed above an adsorbate atom 11 that is bound to the surface 12 of an adsorbent substrate 13. A bias voltage and current of sufficiently low magnitude to prevent unintended movement of atom 11 is applied to tip 10 to initially locate and target the atom on surface 12 by using the STM in conventional imaging mode. Tip 10 is then moved from point A toward atom 11, (e.g., by increasing the tunnel current), until the tip is capable of exerting enough lateral force on the atom to cause the atom to remain located beneath the tip but bound to the substrate when the tip is subsequently moved laterally across the surface. Tip 10 is then moved laterally to point C, (using a conventional STM feedback circuit, not shown, to maintain constant tunneling current), dragging the atom with it along a preselected path to the desired new position. Throughout this lateral movement, the atom remains bound to the surface. At the new position the tip is withdrawn to position D, leaving the atom bound at the new position.

For proper operation, it is necessary to provide a combination of adsorbate atom and substrate surface which will assure that the energy barrier to move from position to position on the surface is smaller than the energy gained by having the atom remain in the region between the tip and substrate. The sign and magnitude of the electric field between the tip and the substrate may be used to change the attractive interaction between the atom and the tip to facilitate the process of dragging an atom across the surface.

In actual test, a Xe atom was dragged from one position to another on the surface of a Pt (111) substrate in the following manner with the atom and substrate disposed in an evacuated 15 container and at a temperature of 4° K.

(1) The Xe atom was targeted and its x,y coordinates determined by applying a current of $1=10^{-11}$ amp. and a negative 0.20 voltage applied to the tip.

(2) The tip was then lowered toward the targeted Xe atom by increasing the demanded tunneling current to $2 \times 10$ amp.

(3) The tip was then moved sequentially in x and then y directions to a new position whose x,y coordinates were preselected, dragging the Xe atom, which remained bound to the Pt surface, en route. This was done with the STM operating in constant current mode at $2\times10^{-10}$ amp.

(4) The tunnel current was then reduced to $1\times10^{-11}$ amp, (the imaging current), and the tip was retracted from the substrate. This effectively terminated the attraction between the Xe atom and the tip, leaving the atom bound to the surface at its new location when the tip was subsequently moved laterally.

While the described experiment was performed considerably below room temperature, the criteria for being able to successfully reposition an atom on a surface using this process are temperature independent. In other words, the lateral, (i.e., in-plane), attractive interaction between the atom and the tip must be sufficiently strong to overcome the energy barrier for an atom to move from site to site along the surface, and the attraction the atom has to the tip must not be so great as to cause the atom to become bound to the tip instead of remaining bound to the surface. Since the energy barrier for moving an atom from site to site across the surface is generally smaller than the atom's adsorption energy, this process will work for a wide range of adsorbate atoms/molecules adsorbed on a wide range of substrates.

II

The method herein described may be used to reposition and attach an atom to one or more other atoms 15 (FIG. 1) of the same or different type at the desired new location. For example, a three terminal atomic scale structure could be fabricated which exhibits the electrical characteristics of a transistor. A molecular compound may be synthesized, for example, by repositioning a C atom to attach to one or more H atoms. This process may be used to fabricate structures which by virtue of their small size exhibit novel behavior or useful properties derived from the nonclassical or quantum mechanical behavior of such small structures.

III

Figure 2:
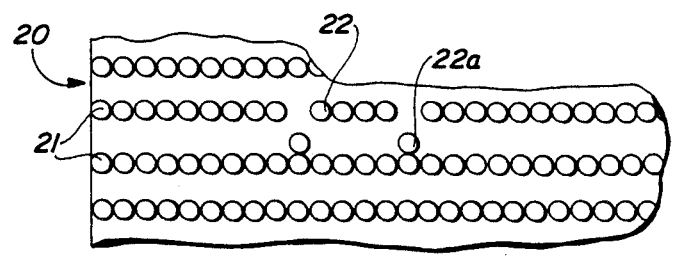
FIG. 2 is a fragmentary view of a recording medium on which data is written using the preferred technique.

The method may also be used to write indicia on a storage medium. As illustrated in FIG. 2, a storage medium 20 in the form of a substrate with an adsorbent surface is provided with a plurality of parallel rows 21 of atoms 22 of similar type. The rows are spaced apart substantially one atom width.

To write indicia, a selectable atom 22a in a selected row is imaged and targeted as above described, and then dragged out of the row into the vacant space between rows while bound to the surface, then released by the tip. After a sequence of these writing steps, the indicia may be read by scanning either each row (or the spaces between rows) sequentially with the tip.

If a substrate with atoms row-arranged is not available, atoms from a supply area of the substrate may be individually dragged and repositioned into rows using the method above described. Or, if preferred, the atoms may be expelled and deposited in a series of parallel rows by an adaptation of the technique described in connection with FIGS. 5 or 6 of the above cited patent to Kazan.

IV

Figure 3:
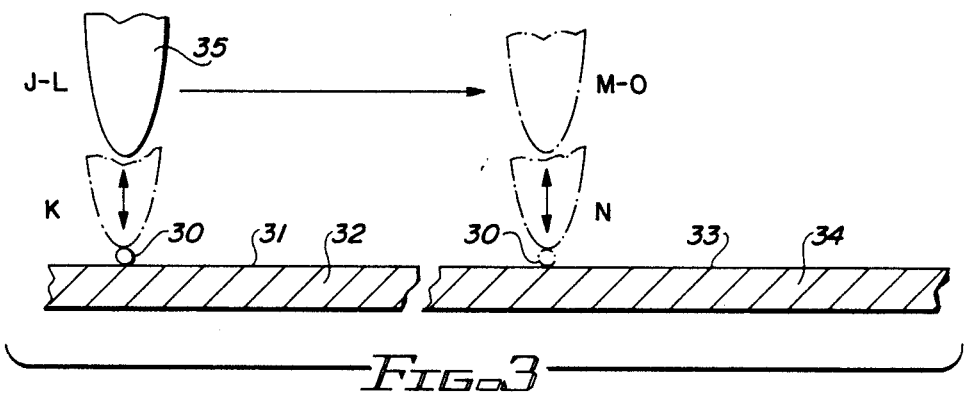
FIG. 3 is a schematic view of an alternative technique for repositioning an atom from one substrate to a different substrate.

FIG. 3 illustrates a method for repositioning a selected atom 30 from surface 31 of one substrate 32 to a surface 33 of another, or the same, substrate 34. STM tip 35 images and targets atom 30 at position J. The tip is then brought to position K such that atom 30 becomes bound to the tip. The tip, with atom attached, is retracted from substrate 32 to position L, then translated to position M above the preselected site at which the atom is to be deposited on surface 33 of substrate 34. The tip 35 is then lowered to position N at which point atom 30 becomes bound to surface 33. The tip is then withdrawn to position O leaving the atom bound to the surface 33.

It will be understood that the applied bias voltage between tip and substrate and the tunneling current may be adjusted so as to facilitate the transfer of the atom to the tip when the tip is at point K and may also be adjusted to facilitate the transfer of the atom from the tip to the surface 33 when the tip is at point N.

It will be understood that, if preferred, the atom 30 can be repositioned on the same substrate 32 or adjacent another atom (like 15 in FIG. 1) to fabricate a device, such as an electrical component, or synthesize a chemical compound, as described in connection with FIG. 1.

It is to be noted that the prior art does not teach or suggest repositioning a selected atom by use of a STM.

While the invention has been particularly shown and described with reference to preferred embodiments thereof, it will be understood by those skilled in the art that various changes in form and details ma be made therein without departing from the spirit and scope of the invention. Accordingly, the method herein disclosed is to be considered merely as illustrative and the invention is to be limited only as specified in the claims.

I claim:

1. A method for repositioning an adsorbate atom on a substrate surface, comprising the steps of:

moving the tip of a STM to a position proximate the atom to be moved and then increasing the attraction between the tip and atom by moving the tip closer to the atom; and while the atom remains bound to the surface, moving the tip laterally to drag the atom to a desired position on the surface.

2. The method of claim 1, wherein during the moving step the tip is moved to a position adjacent the atom to be moved and the tunnel current is concurrently increased to create an attraction between the tip and atom.

3. The method of claim 1, including the step of:

moving the tip away from the substrate so as to reduce the attraction between the atom and tip and leave the atom bound at said desired position.

4. The method of claim 1, including the step of:

reducing the tunnel current to terminate the attraction between the atom and tip and leave the atom bound at said desired position.

5. The method of claim 1, including the step of:

providing at least one other atom bound to the surface and to which the first-mentioned atom is attached when in said desired position.

6. The method of claim 5, wherein the first-mentioned atom is of a different type than at least one of said other atoms.

7. A method of repositioning atoms for fabricating a desired multi-atom structure on a substrate, comprising the steps of:

providing at least one atom of one type; and using a STM, repositioning each such atom in sufficiently close proximity to an atom of another type on the substrate to create the structure.

8. The method of claim 7, wherein the atoms of both types are on the substrate, and the repositioning is effected by moving each atom of said one type into proximity with at least one of the other type.

9. The method of claim 7, wherein the atoms of both types are on the substrate, and the repositioning step includes the steps of:
   using said tip, imaging each atom of said one type individually to target such atom;
   activating the tip to attract the targeted atom toward it while the atom remains bound to the substrate;
   moving the tip laterally for dragging the targeted atom in a preselected path on said substrate into proximity with the atom of the other type; and
   deactivating the tip to free the targeted atom so the atoms of the respective types will remain bonded to the substrate in their respective proximate positions.

10. The method of claim 7, including, during the repositioning step, the steps of:
    moving the tip of the STM to a position above an atom of said one type while applying a bias voltage/current thereto to image and target the atom as being of said type;
    lowering the tip into proximity with, but at one side of, the targeted atom;
    increasing the bias voltage/current in a direction sufficient to cause the targeted atom to be drawn into a high field region between the tip and substrate;
    moving the tip along the substrate and concurrently dragging the targeted atom in a preselected path with the tip to a desired position in proximity with the atom of said other type while the latter atom remains bound to the substrate; and
    reducing the bias voltage/current to cause the targeted atom to remain bound at said desired position.

11. The method of claim 7, wherein the structure is an electrical component comprising at least one donor element and at least one receptor element.

12. A method of repositioning a plurality of adsorbate atoms on a substrate surface to write indicia on a storage medium, comprising the steps of:
    providing a plurality of parallel rows of said atoms spaced approximately one atom width apart on the medium;
    moving the tip of a STM to a position adjacent the atom to be moved and concurrently increasing the tunnel current to create an attraction between the tip and atom; and
    while the atom remains bound to the surface, moving the tip transversely of the rows to drag a selected atom from its respective row into the adjacent vacant space; and
    repeating the moving steps to remove atoms at selected locations along the respective rows to thereby write indicia as denoted by the removed atoms.

13. A method of repositioning atoms to synthesize a molecule comprising the steps of
    providing at least one adsorbent atom of one type; and
    using a STM, repositioning each such atom in physical contact with an atom of a different type to create the synthesized molecule.

14. A method of repositioning an atom using a STM having a tip, comprising the steps of:
    providing a substrate to which the atom is bound;
    targeting the atom on the substrate with the tip;
    placing the tip in such close proximity to the atom that the atom becomes bound to the tip and remains bound to the tip when the tip is withdrawn from the substrate;
    withdrawing the tip from the substrate;
    moving the tip generally laterally to a desired position above said or another substrate;
    lowering the tip at said position until the atom becomes preferentially bound to the substrate at the desired location; and
    withdrawing the tip from the substrate-bound atom leaving the atom at the desired location on the surface of the selected substrate.

15. A method of repositioning an atom using a STM having a tip, comprising the steps of:
    providing a substrate to which the atom is bound;
    targeting the atom on the substrate with the tip;
    moving the tip to a position adjacent the atom;
    changing the bias voltage/current sufficient to cause the atom to become attached to the tip; while maintaining the changed bias voltage/current,
    raising the tip from the substrate;
    moving the tip generally laterally to a desired position above said substrate; and
    lowering the tip at said position into proximity with the substrate; and
    altering the bias voltage/current at said desired position to cause said atom to be repositioned on said substrate at said position.

* * * * *